(12) United States Patent
Mendez

(10) Patent No.: US 9,067,028 B2
(45) Date of Patent: Jun. 30, 2015

(54) INJECTION DELIVERY SYSTEM

(71) Applicant: Ivar Mendez, Lucasville (CA)

(72) Inventor: Ivar Mendez, Lucasville (CA)

(*) Notice: Subject to any disclaimer, the term of this patent is extended or adjusted under 35 U.S.C. 154(b) by 0 days.

(21) Appl. No.: 14/305,310

(22) Filed: Jun. 16, 2014

(65) Prior Publication Data

US 2014/0296783 A1 Oct. 2, 2014

Related U.S. Application Data

(63) Continuation of application No. 12/368,858, filed on Feb. 10, 2009, now Pat. No. 8,753,314.

(60) Provisional application No. 61/064,027, filed on Feb. 11, 2008.

(51) Int. Cl.
| | | |
|---|---|---|
| *A61M 5/00* | (2006.01) | |
| *A61M 5/46* | (2006.01) | |
| *A61B 19/00* | (2006.01) | |
| *A61M 5/20* | (2006.01) | |
| *A61B 17/00* | (2006.01) | |
| *A61M 5/32* | (2006.01) | |
| *A61B 17/34* | (2006.01) | |

(52) U.S. Cl.
CPC ......... *A61M 5/46* (2013.01); *A61M 2005/3289* (2013.01); *A61B 19/2203* (2013.01); *A61B 2017/3409* (2013.01); *A61M 5/20* (2013.01); *A61M 2005/206* (2013.01); *A61B 17/0057* (2013.01); *A61B 2017/0065* (2013.01); *A61B 19/56* (2013.01); *A61B 2019/568* (2013.01); *A61M 2205/10* (2013.01); *A61M 2210/00* (2013.01)

(58) Field of Classification Search
CPC . A61M 5/20; A61M 5/46; A61M 2005/3289; A61M 5/326; A61M 2005/206; A61M 2210/0693; A61M 2205/10
See application file for complete search history.

(56) References Cited

U.S. PATENT DOCUMENTS

| | | | |
|---|---|---|---|
| 4,333,459 A | 6/1982 | Becker | |
| 4,563,175 A | 1/1986 | LaFond | |
| 4,613,328 A | 9/1986 | Boyd | |
| 4,790,823 A | 12/1988 | Charton et al. | |
| 5,578,014 A | 11/1996 | Erez et al. | |
| 6,183,442 B1* | 2/2001 | Athanasiou et al. | 604/154 |
| 7,025,774 B2 | 4/2006 | Freeman et al. | |

(Continued)

FOREIGN PATENT DOCUMENTS

CA 2282007 A1 1/2001

*Primary Examiner* — Kevin C Sirmons
*Assistant Examiner* — William Carpenter
(74) *Attorney, Agent, or Firm* — Steven M. Greenberg; CRGO Law

(57) ABSTRACT

An injection delivery system for automatically injecting fluid into an injection site includes at least one support element and a carriage moveably mounted to the at least one support element so that the carriage can move linearly relative thereto. The carriage has a support structure for removably receiving and carrying a syringe assembly for movement with the carriage, and a carriage actuator is operable to cause such linear movement of the carriage. A plunger actuator is carried by the carriage so as to move with the carriage, and is adapted to be operably coupled to a syringe plunger for causing linear movement of the syringe plunger within a syringe barrel. The carriage actuator and plunger actuator include respective inputs for receiving movement instructions, and may be coupled to an electronic controller that provides such instructions.

6 Claims, 5 Drawing Sheets

(56) References Cited

U.S. PATENT DOCUMENTS

| | | |
|---|---|---|
| 7,137,969 B1 | 11/2006 | Mendez |
| 7,494,494 B2 | 2/2009 | Stoianovici et al. |
| 8,753,314 B2 | 6/2014 | Mendez |
| 2004/0254525 A1 | 12/2004 | Uber, III et al. |

* cited by examiner

INJECTION DELIVERY SYSTEM

CROSS-REFERENCE TO RELATED APPLICATION

This application is a Continuation of and claims priority to U.S. application Ser. No. 12/368,858 filed on Feb. 10, 2009 and entitled "INJECTION DELIVERY SYSTEM," which claims priority to U.S. Provisional Patent Application No. 61/064,027 filed on Feb. 11, 2008, the teachings of which are hereby incorporated by reference.

BACKGROUND OF THE INVENTION

In many instances, it is considered (or may, due to advancements in medical science, be considered in the future) to be necessary or advantageous to inject certain substances, such as medications or suspensions of organic matter such as cells, into the human body. Often, such injections require relatively high levels of precision, both in terms of the precise location (or locations) within the body at which the relevant substance is administered, and also in terms of the quantity of the substance and the rate of delivery thereof.

Canadian Patent No. 2,282,007 describes a neural transplantation delivery system. The neural transplantation delivery system includes a threaded plunger driver which cooperates with a threaded drive nut to control movement of a plunger so as to control the metered administration of a fluid, and also includes a threaded guide nut which rotates within a threaded plunger guide to effect linear movement (insertion and withdrawal) of a syringe and attached transplantation cannula. In particular, rotation of the guide nut translates to linear movement of the syringe and cannula. The nature of this arrangement requires that the threaded drive nut and guide nut be co-rotated precisely during insertion and withdrawal of the cannula to avoid relative movement of the syringe barrel and the plunger. Also disclosed is a cannula having a closed tip and diametrically opposed offset holes to effect deposition of fluid in a spiral pattern as a result of the rotation of the cannula during withdrawal from an injection site.

Canadian Patent No. 2,282,007 corresponds to U.S. Pat. No. 7,137,969, and both of these documents are hereby incorporated by reference in their entirety.

Both the threaded drive nut and the guide nut of the neural transplantation delivery system described in Canadian Patent No. 2,282,007 must be manually rotated by the surgeon. Because the threaded drive nut and guide nut of the neural transplantation delivery system described in Canadian Patent No. 2,282,007 must be co-rotated precisely during insertion and withdrawal of the cannula to avoid relative movement of the syringe barrel and the plunger, there is a risk of adverse effects, such as unintentional injection of fluid, or unintentional withdrawal of fluid, if the synchronization is not sufficiently precise. In addition, precision in the amount of fluid administered is limited by the surgeon's manual dexterity.

SUMMARY OF THE INVENTION

In one aspect, the present invention is directed to an injection delivery system for automatically injecting fluid into an injection site. The injection delivery system comprises at least one support element, a carriage moveably mounted to the at least one support element so that the carriage can move linearly relative to the at least one support element, and a carriage actuator operable to cause linear movement of the carriage relative to the at least one support element. A syringe assembly is carried by the carriage so as to move with the carriage. The syringe assembly comprises a syringe barrel defining an interior volume for receiving a fluid, a cannula in fluid communication with the syringe barrel, the cannula being positioned parallel to the direction of linear movement of the carriage, and a plunger slidably received within the syringe barrel. A plunger actuator is carried by the carriage so as to move with the carriage, and is operably coupled to the plunger for causing linear movement of the plunger within the syringe barrel. The injection delivery system further comprises an electronic controller for controlling the carriage actuator and the plunger actuator according to instructions stored on a computer readable medium.

In one embodiment, the electronic controller comprises a user interface for changing the instructions on the computer readable medium, which may be a touch screen device.

In one embodiment, the cannula is rotatable relative to the carriage, and the injection delivery system further comprises a rotation actuator operable for causing rotation of the cannula relative to the carriage. The electronic controller may control the rotation actuator according to instructions stored on a computer readable medium.

The instructions on the computer readable medium may include at least one of (a) at least one volume of fluid to impart from the cannula; (b) an insertion distance that the cannula moves in relation to the at least one support element in the direction of the injection site; (c) a retraction distance that the cannula retracts in relation to the at least one support element from the injection site; (d) a rotation amount that the cannula rotates in relation to the carriage after a particular injection; and (e) a pause time that the cannula will remain still after a particular injection.

The above-described injection delivery system may be used to implement a method of automatically controlling the injection of fluid into an injection site using the electronic controller according to instructions stored on a computer readable medium. Such a method may comprise inserting the cannula into the injection site by the insertion distance according to the instructions, implanting a first volume of fluid through the cannula, the first volume according to the instructions, and retracting the cannula by the retraction distance according to the instructions. The method may further include rotating the cannula by the rotation amount according to the instructions, retracting the cannula by a retraction gap distance, and implanting a second volume of fluid through the cannula, the second volume according to the instructions, before retracting the cannula. The method may still further include pausing movement of the cannula for the pause time according to the instructions, after the step of implanting the first volume of fluid. The instructions may be provided by a user via a user interface of the electronic controller.

In another aspect, the present invention is directed to an injection delivery system for automatically injecting fluid into an injection site. The injection delivery system comprises at least one support element, and a carriage moveably mounted to the at least one support element so that the carriage can move linearly relative to the at least one support element. The carriage has a support structure for removably receiving and carrying a syringe assembly for movement with the carriage. A carriage actuator is operable to cause linear movement of the carriage relative to the at least one support element, and includes a carriage actuator input for receiving carriage movement instructions. A plunger actuator is carried by the carriage so as to move with the carriage, and is adapted to be operably coupled to a syringe plunger for causing linear movement thereof within a syringe barrel. The plunger actuator includes a plunger actuator input for receiving plunger movement instructions.

In one embodiment, the injection delivery system includes a rotation actuator operable for causing rotation of a cannula relative to the carriage, and the rotation actuator includes a rotation actuator input for receiving rotation instructions.

The injection delivery system may further comprise an electronic controller for controlling the carriage actuator by providing the carriage movement instructions via the carriage actuator input, controlling the plunger actuator by providing the plunger movement instructions via the plunger actuator input, and controlling the rotation actuator by providing the rotation instructions via the rotation actuator input. The electronic controller may include a user interface, which may be a touch screen device, and the carriage movement instructions, plunger movement instructions and rotation instructions may be stored on a computer readable medium accessible by the electronic controller. The carriage movement instructions, the plunger movement instructions and the rotation instructions may be derived from (a) a volume of fluid to impart from the cannula; (b) an insertion distance that the cannula moves in relation to the at least one support element in the direction of the injection site; (c) a retraction distance that the cannula retracts in relation to the at least one support element from the injection site; (d) a rotation amount that the cannula rotates in relation to the carriage after a particular injection; and (e) a pause time that the cannula will remain still after a particular injection.

In yet another aspect, the present invention is directed to an injection delivery system. The injection delivery system includes at least one support element, and a carriage moveably mounted to the at least one support element so that the carriage can move linearly relative to the at least one support element. A carriage actuator is operable to cause linear movement of the carriage relative to the at least one support element. A syringe assembly is coupled to the carriage so as to move with the carriage. The syringe assembly comprises a syringe barrel defining an interior volume for receiving a fluid, a cannula in fluid communication with the syringe barrel, with the cannula being positioned parallel to the direction of linear movement of the carriage, and a plunger slidably received within the syringe barrel. A plunger actuator is operably coupled to the plunger for causing linear movement of the plunger within the syringe barrel.

In one embodiment, the cannula is rotatable relative to the carriage, and a rotation actuator is operable for causing rotation of the cannula relative to the carriage.

The carriage may comprise a movable element of a first linear actuator and the at least one support element may comprise a frame of the first linear actuator. The plunger actuator may comprise a second linear actuator.

BRIEF DESCRIPTION OF THE DRAWINGS

In order that the subject matter may be readily understood, embodiments are illustrated by way of examples in the following drawings, in which.

DETAILED DESCRIPTION

Figure 1:
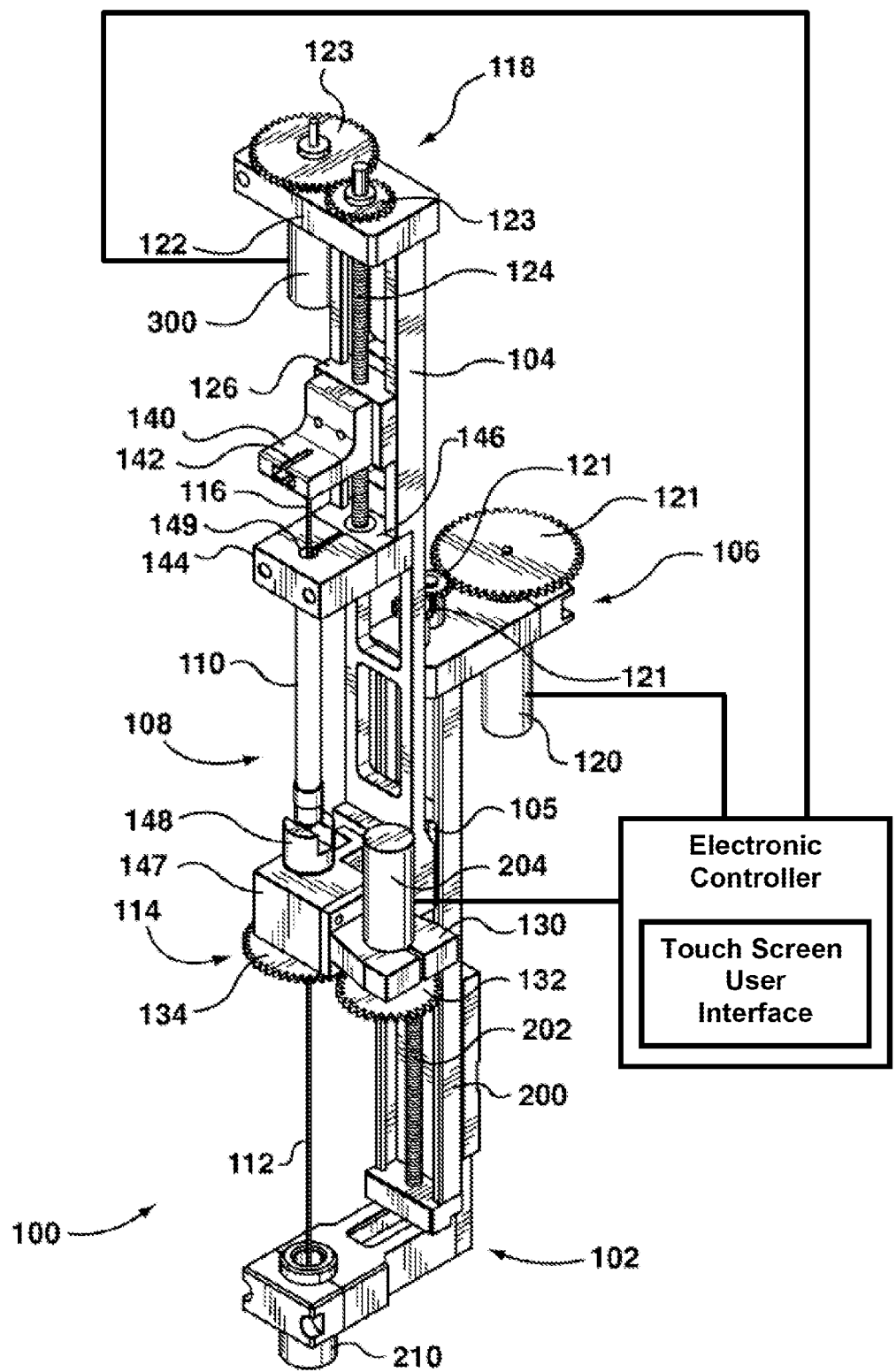
FIG. 1 is a perspective view of an exemplary embodiment of an injection delivery system in accordance with an aspect of the present invention.

Referring now to FIG. 1, an injection delivery system is shown generally at 100. The injection delivery system 100 comprises a support element 102, a carriage 104 and a carriage actuator 106. As will be described in greater detail below, the carriage 104 is movably mounted to the support element 102 so that the carriage 104 can move linearly relatively to the support element 102, and the carriage actuator 106 is operable to drive such linear movement of the carriage 104. Thus, the carriage 104 may comprise a movable element of a first linear actuator and the at least one support element 102, or a plurality of support elements, may comprise a frame of the first linear actuator.

A syringe assembly 108 may be mounted on the carriage 104. As shown in FIG. 1, the exemplary syringe assembly 108 includes a syringe barrel 110, a cannula 112 and a plunger 116 slidably received within the syringe barrel 110. The syringe barrel 110 defines an interior volume, which can receive a fluid. The cannula 112 is in fluid communication with the syringe barrel, and is positioned so as to be longitudinally parallel to the direction of linear movement of the carriage. The cannula 112 may be provided with a standard Luer lock at one end, which allows the cannula 112 to be readily attached to and in fluid connection with the syringe barrel 110.

The cannula 112 may be any one of a variety of different types of cannula, depending on the operation being performed. For example, for a cannula as described in Canadian Patent No. 2,282,007, the tip of the cannula 112 at the end opposite the syringe barrel 110 is closed and its outer surface is rounded and polished in a semi-spherical shape (not shown) to minimize trauma to neural tissue upon insertion, and near the closed tip of the cannula is a pair of holes to allow egress of fluids (e.g. a cell suspension) during aspiration of the syringe, with the holes being diametrically opposed and slightly offset to one another. In other embodiments, the cannula 112 may be a conventional needle, or may be of another type adapted to a particular type of surgery.

Figure 2:
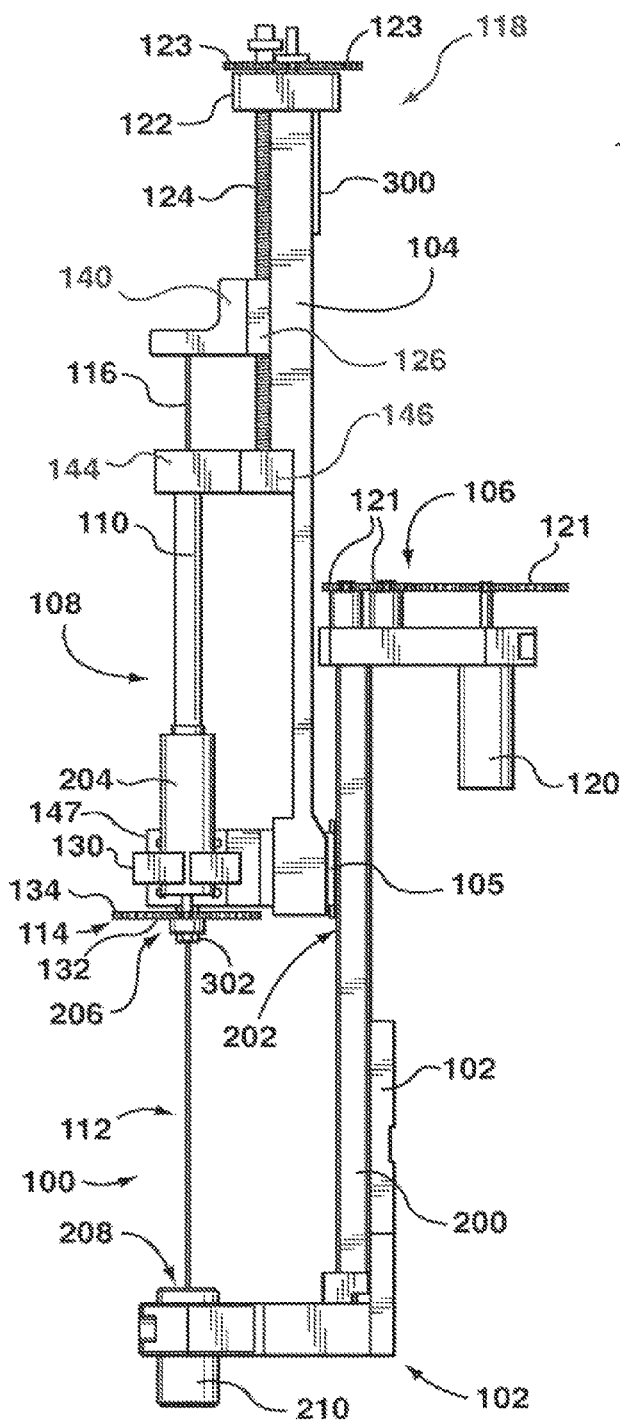
FIG. 2 is a side view of the injection delivery system of FIG. 1.
Figure 3:
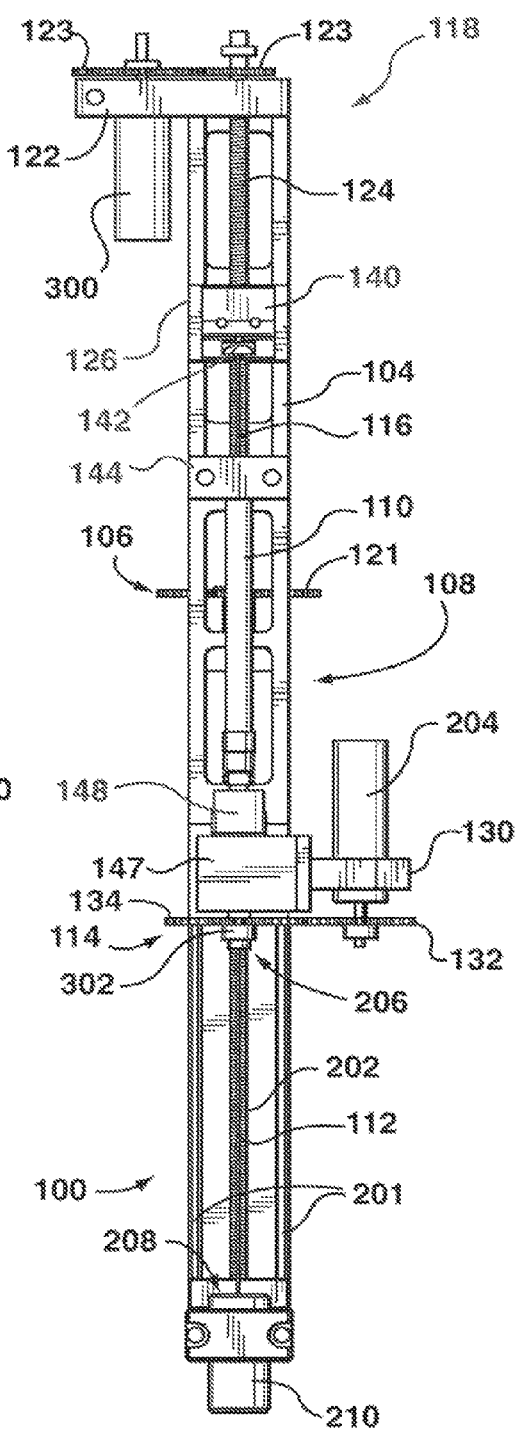
FIG. 3 is front view of the injection delivery system of FIG. 1.

Referring now to FIGS. 2 and 3, in the illustrated embodiment the support element 102 comprises a frame 200 having opposed guide walls 201 (FIG. 3) and having a rotatable carriage actuator threaded rod 202 disposed between the opposed guide walls 201. A frame mounting portion 105 of the carriage 104 is slidably received between the opposed guide walls 201 and contains a threaded aperture (not shown) that is threadingly engaged with the carriage actuator threaded rod 202. As such, the carriage 104 is slidably mounted on the frame 200 and is threadingly engaged with the carriage actuator threaded rod 202, so that rotation of the carriage actuator threaded rod 202 will drive linear movement of the carriage 104 along the frame 200. The frame 200 may be shaped as in the embodiment depicted in the Figures, or may have other suitable shapes.

As shown in FIGS. 1 and 2, the carriage actuator 106 comprises a carriage motor 120, gears 121 and the carriage actuator threaded rod 202. The carriage motor 120 is supported by the frame 200 and operatively connected to the carriage actuator threaded rod 202, in the illustrated embodiment by way of the gears 121, so that the carriage motor 120 can drive rotation of the carriage actuator threaded rod 202, and thus cause linear movement of the carriage 104 relative to the frame 200. More particularly, in operation of the carriage actuator 106, the carriage motor 120 rotates the carriage actuator threaded rod 202, thereby causing the frame mounting portion 105, and hence the carriage 104, to move linearly along the frame 200. Other types of carriage actuator may also be used.

In the embodiment shown in the Figures, a plunger 116 is slidably received within the syringe barrel 110 at an end opposite the cannula 112, and is sized to fit into the syringe barrel 110 such that a seal forms between the plunger 116 and the internal wall(s) of the syringe barrel 110. To this end, a seal member (not shown) may be provided on the plunger. Accordingly, movement of the plunger 116 toward the end of the syringe barrel 110 carrying the cannula 112 will cause fluid contained in the syringe barrel 110 to be expelled through the cannula 112.

A plunger actuator 118 is operably coupled to the plunger 116 for causing linear movement of the plunger 116 within the syringe barrel 110. The plunger actuator may comprise a second linear actuator. Referring to FIG. 1, in the illustrated embodiment the plunger actuator 118 comprises a plunger motor 300, a plunger actuator frame 122, a plunger actuator threaded rod 124 and a moveable element 126 having a threaded aperture (not shown) which threadingly receives the plunger actuator threaded rod 124. The plunger actuator frame 122 is secured to the carriage 104 at an end thereof opposite the intended position of the cannula 112, and the movable element 126 is slidingly received in the carriage 104. One end of the plunger actuator threaded rod 124 is rotatably received in the plunger actuator frame 122, and the other end of the plunger actuator threaded rod 124 is rotatably received in a support plate 146 secured to the carriage 104. The plunger motor 300 is attached to the plunger actuator frame 122, and is operable to drive the plunger actuator threaded rod 124 by way of gears 123 rotatably mounted on the plunger actuator frame 122. One of the gears 123 is coaxially mounted on the plunger actuator threaded rod 124. Because the movable element 126 is slidably received in the carriage 104 and threadingly receives the plunger actuator threaded rod 124, rotation of the plunger actuator threaded rod 124 translates to linear movement of the movable element along the carriage 104. The plunger 116 is secured to the moveable element 126 so that linear movement of the movable element 126 causes corresponding linear movement of the plunger 116. In operation of the plunger actuator 118, the plunger motor 300 rotates the plunger actuator threaded rod 124, thereby causing the moveable element 126 to move linearly along the carriage 104, which in turn moves the plunger 116 into the syringe barrel 110, thereby forcing fluid from the syringe barrel 110 into the cannula 112. Other types of plunger actuator may also be used.

In the illustrated embodiment, the carriage 104 has a support structure for removably receiving and carrying the syringe assembly 108 for movement with the carriage 104, so that the syringe assembly 108 can be removed for cleaning, or for replacement with another syringe assembly 108 (e.g. where the syringe assembly is disposable). More particularly, the movable element 126 carries an L-shaped plunger receiving bracket 140 which has a slot 142 for receiving the tip of the plunger, so that linear movement of the moveable element 126 causes linear movement of the plunger 116. A first syringe barrel mounting bracket 144 having a recess 149 for receiving the plunger end of a syringe (such as syringe barrel 110) is removably secured to the support plate 146, and a second syringe barrel mounting bracket 148 for receiving the cannula end of a syringe is secured to a rotation support 147, which is in turn secured to the carriage 104. Thus, by removing the first syringe barrel mounting bracket 144, a syringe assembly (such as syringe assembly 108) can be removed from and/or installed on the carriage 104.

In the illustrated embodiment, the plunger actuator 118 forms part of the carriage 104. In other embodiments, a plunger actuator may be integrated with a syringe assembly 108, so that the combined syringe assembly/plunger actuator can be installed on and removed from the carriage 104 as a single unit. For example, the plunger actuator and syringe assembly may be mounted on a common platform that is mounted to the carriage 104. Alternatively the plunger actuator may be a separate component that is removably mounted to the carriage 104. The plunger actuator may be located elsewhere so long as it is operably connected to the plunger 116 (i.e. so that the plunger actuator 118 operates to move the plunger 116 linearly along the longitudinal axis of the syringe assembly 108 within the interior volume of the syringe barrel 110).

Figure 4:
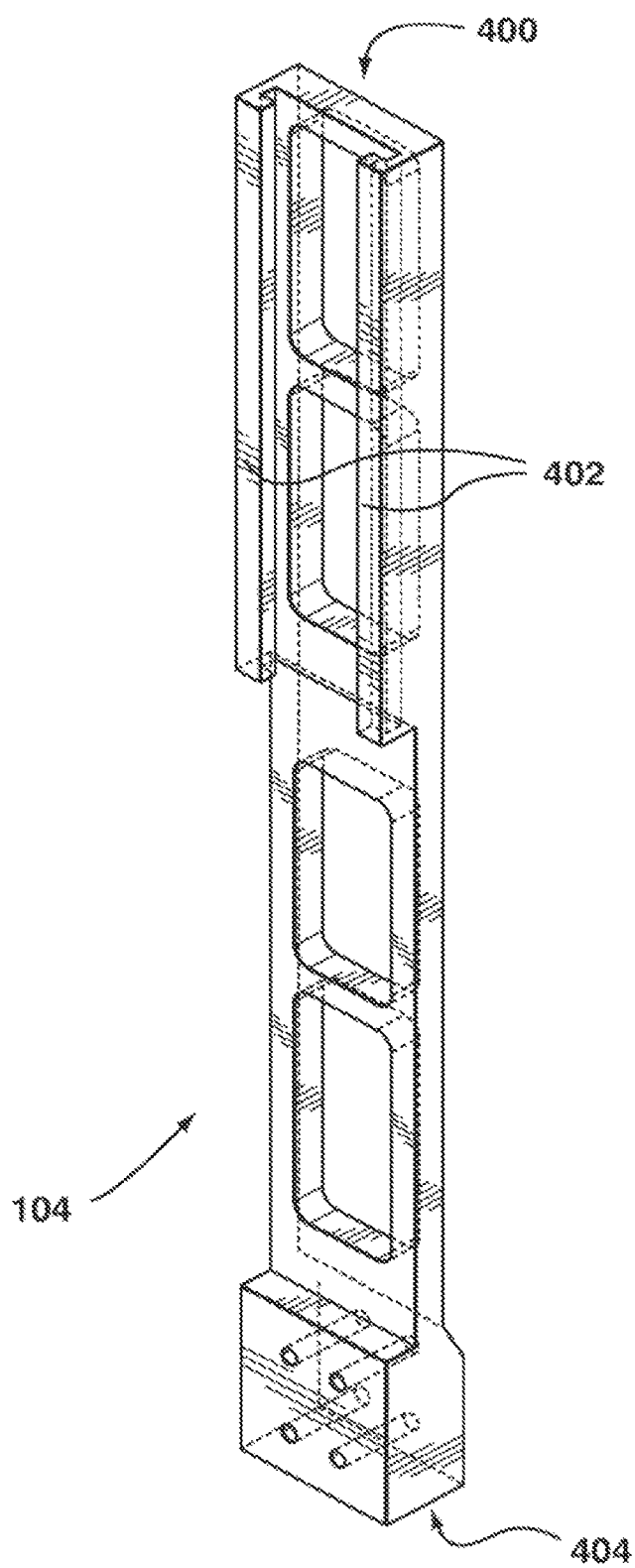
FIG. 4 is a perspective view of a carriage of the injection delivery system of FIG. 1.

The embodiment of the carriage 104 depicted in FIGS. 1 to 3 is shown in more detail in FIG. 4. The plunger actuator frame 122 (not shown in FIG. 4) attaches at the top end 400 of the carriage 104, and two opposed parallel side walls 402 extend along the carriage 104 from the top end 400. The moveable plunger element 126 (not shown in FIG. 4) slidingly engages with the side walls 402, so that rotation of the plunger actuator threaded rod 124 (not shown in FIG. 4) causes the moveable element 126 to slide rather than rotate relative to the carriage 104, as described above. The frame mounting portion 105 (not shown in FIG. 4) is secured to the carriage 104 at the bottom end 404 thereof, on the opposite side of the carriage 104 from the side walls 402.

Referring again to FIGS. 1 to 3, in the illustrated embodiment, the cannula 112 is rotatable relative to the carriage 104, and the injection delivery system 100 further comprises a rotation actuator 114 operable for causing incremental rotation of the cannula 112 relative to the carriage 104. The rotation actuator 114 comprises a motor mounting 130, a rotation motor 204, gears 132, 134, and a rotation attachment 302 (FIGS. 2 and 3). The rotation motor 204 is mounted to the motor mounting 130, which is attached to the rotation support 147 secured to the carriage 104. The rotation attachment 302 grips the cannula 112, and is rotatably secured to the rotation support 147 co-axially with an aperture (not shown) in the rotation support 147 for the cannula 112. The rotation motor 204 operates to turn a first gear 132 which is interlocked with a second gear 134, with the second gear 134 being co-axially mounted to the rotation attachment 302. Accordingly, the rotation motor 204 drives rotation of the rotation attachment 302 and hence rotation of the cannula 112 about its longitudinal axis, relative to the carriage 104. As can be seen in FIGS. 1 to 3, the rotation actuator 114 is carried by the carriage 104 so that the rotation actuator 114 can rotate the cannula 112 without causing linear movement of the syringe assembly 108 and the included cannula 112.

To achieve rotation of the cannula 112 relative to the carriage 104, the rotation actuator 114 can be configured so that the cannula 112 rotates relative to the syringe barrel 110, or so that both the cannula 112 and the syringe barrel 110 rotate relative to the plunger 116, or so that the entire syringe assembly 108 rotates relative to the carriage, so long as the configuration includes an arrangement for sufficiently inhibiting leakage of fluid from the syringe assembly. Referring to FIGS. 2 and 3, the end 206 of the cannula 112 that is proximal to the syringe barrel 110 is gripped by the rotation attachment 302, and the end 206 of the cannula 112 that is distal from the syringe barrel 110 is received at a second end 208 in a guide 210.

Figure 5:
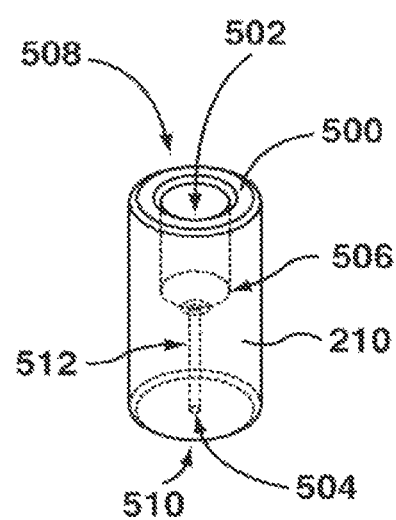
FIG. 5 is a perspective view of a guide of the injection delivery system of FIG. 1.

One embodiment of the guide 210 is shown in more detail in FIG. 5. The guide 210 has a top end 508 for receiving the cannula 112 and a bottom end 510 through which the cannula 112 extends. The top end 508 of the guide 210 has a rim 500 surrounding a cavity 502. The cavity 502 tapers at a shoulder 506 to a narrow passage 512 terminating at an exit aperture 504. The narrow passage 512 is sized to precisely or snugly fit the cannula 112 to assist in supporting accuracy of injection.

Figure 7:
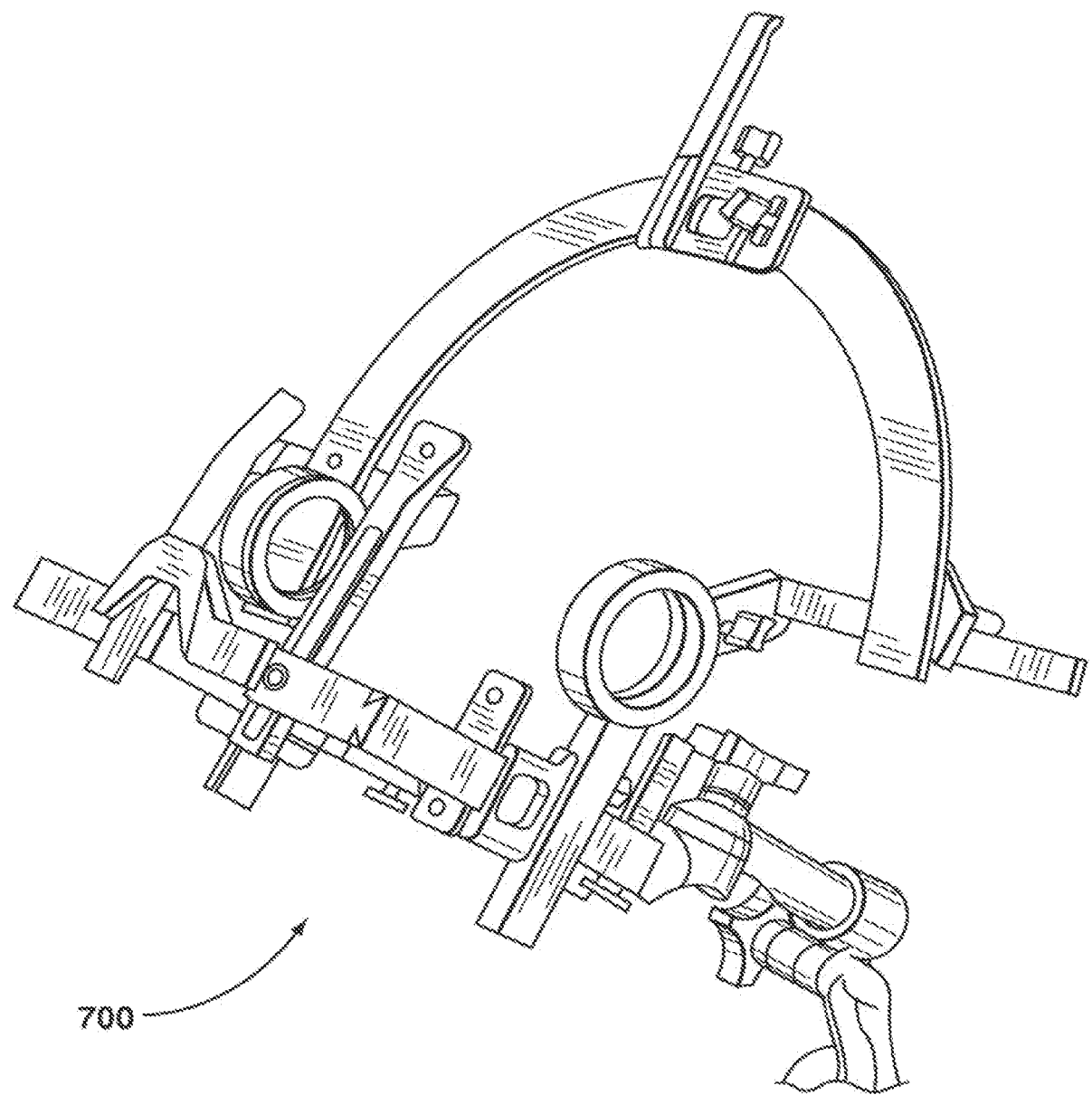
FIG. 7 is a perspective view of a stereotactic frame.

The frame 102 may be mounted, for example by way of a Leskell adaptor or a stereotactic arc adapter, to a stereotactic frame 700 such as that shown in FIG. 7, so that the injection delivery system 100 may be used in stereotactic neurosurgery. Such mounting is within the capability of one skilled in the art, once informed by the herein disclosure. The carriage actuator 106 enables insertion of the cannula 112 into, and retraction of the cannula 112 from, an injection site of a patient, along a linear path. The plunger actuator 118 enables movement of the plunger 116 for metered administration of the contents of the syringe barrel 110. The rotation actuator 114 rotates the cannula 112 within the injection site. The carriage actuator 106 and the rotation actuator 114 can cooperate (either by simultaneous movement or discrete sequential movements) to rotate the cannula 112 during insertion into or withdrawal from an injection site, and thereby achieve patterns of deposition, such as the spiral pattern of deposition described in Canadian Patent No. 2,282,007. Rotation of the cannula 112 may be, for example, in 90 degree increments.

While particular exemplary implementations have been described above, the carriage actuator 106, plunger actuator 118 and (if included) rotation actuator 114 may be any suitable mechanical actuator arrangement (e.g. motors, gears and the like) having sufficient precision to achieve the required small amounts of movement.

In a preferred embodiment, the carriage actuator 106, plunger actuator 118 and (if included) rotation actuator 114 are each controlled electronically, for example by one or more purpose-built controllers, or by one or more suitably programmed general-purpose computers. As such, the carriage actuator 106 includes a carriage actuator input (not shown) for receiving carriage movement instructions, the plunger actuator 118 has a plunger actuator input (not shown) for receiving plunger movement instructions, and the rotation actuator 114 has a rotation actuator input (not shown) for receiving rotation instructions. The electronic controller may be connected to the input of the relevant actuator (carriage actuator 106, plunger actuator 118, rotation actuator 114) by suitable interface cables, as will be apparent to one skilled in the art, once informed by the herein disclosure. Alternatively, for procedures where manually obtainable precision is considered sufficient for operation of the plunger and rotation of the cannula (if such is provided for), only the carriage actuator 106 need be controlled electronically.

The electronic controller sends signals to operate the relevant actuator (carriage actuator 106, plunger actuator 118, rotation actuator 114) in order to control the operation of the injection delivery system 100.

To control insertion and retraction of the cannula 112, the electronic controller will send signals to the carriage actuator 106. For example, the electronic controller may send a signal to rotate the carriage motor 120 in a first rotational direction, which, by way of gears 121, rotates the carriage actuator threaded rod 202 and hence moves the carriage 104 and the cannula 112 in a first linear direction. The first linear direction may, for example, correspond to insertion of the cannula into a patient. The electronic controller may also send signals to stop or pause rotation of the carriage motor 120 (and hence stop or pause the linear movement of the cannula 112), thus, the carriage actuator is operable to cause incremental linear movement of the carriage 104 relative to the support element 102. The electronic controller may also send signals to rotate the carriage motor 120 in a second rotational direction opposite the first rotational direction, and hence move the carriage 104 and the cannula 112 in a second linear direction opposite the first linear direction, which may, for example, correspond to a retraction of the cannula 112 from the patient.

To control administration of fluid contained in the syringe barrel 110 through the cannula 112, the electronic controller sends signals to the plunger actuator 118. Signals from the electronic controller will activate the plunger motor 300, which in turn rotates the gears 123 and the plunger actuator threaded rod 124, translating to linear movement of the movable element 126 along the carriage 104 and hence linear movement of the plunger 116 within the syringe barrel 110. Where a fluid is being administered, movement of the plunger 116 should only be in the direction of the cannula 112, and hence in such situations the plunger motor 300 will only rotate in one direction. The plunger actuator 118 is thereby operably coupled to the plunger for causing incremental linear movement of the plunger 116 within the syringe barrel 110.

To control rotation of the cannula 112, the electronic controller will send signals to operate the rotation actuator 114. For example, a signal from the electronic controller may activate the rotation motor 204 to rotate in a first rotational direction, which will, via gears 132 and 134, rotate the rotation attachment 302 and thus rotate the cannula 112. Similarly, a signal from the electronic controller to the rotation motor 204 to rotate in the opposite direction will rotate the cannula 112 in the opposite direction.

In one embodiment, the electronic controller has a user interface, which may for example be a touch-screen (see FIG. 1). The touch-screen or other user interface can for example be draped for use by a surgically sterile operator. The user interface allows a user to provide instructions to the electronic controller and/or change instructions already programmed into the controller.

Use of an electronic controller allows an injection delivery system according to an aspect of the present invention, such as the injection delivery system 100, to operate with a high degree of precision. Levels of precision, as well as other specifications, considered desirable for neurosurgery include the following:

Delivery accuracy: +/−0.1 microliters (100 nanoliters)
Total volume capacity: 50 microliters
Volume feedback accuracy: 50 nanoliters
Position accuracy: 50 micrometers
Position feedback accuracy: 50 nanometers
Injection speed: 1.0 microliter/min
Position speed between implants: 1.0 mm/sec
Pre and post implant speed: 3.0 mm/sec In one embodiment, a programmable electronic controller for the injection delivery system 100 provides for automated operation in association with certain parameters. Thus, the electronic controller can control the injection delivery system 100 to deliver a fluid according to a predetermined pattern, for example as taught by Canadian Patent No. 2,282,007. In such a mode of operation, the electronic controller would provide instructions to the relevant actuators (carriage actuator 106, plunger actuator 118, rotation actuator 114) for insertion, injection, rotation, and retraction along the extent of an insertion path into a target injection site. All such operations (e.g.

insert, inject, rotate and retract) may be pre-programmed as a sequence into the electronic controller. Such a sequence of operations may be stored by a computer readable medium, which may form part of the electronic controller or may be otherwise accessible thereby. For example, the instructions may be programmed using a user interface. The instructions will typically include, or be derived from, specific operational parameters. For example, such operational parameters may include the following:

(a) Cannula Insertion: This parameter reflects how far the cannula 112 has to move to reach the initial target of the injection site, and it may be marked in millimeters.

(b) Implant Volume: This parameter reflects the volume of each implant (i.e. each fluid administration) that will be performed during the operation, and it may be marked in microliters.

(c) Retraction Gap: This parameter reflects the distance between each implant as the cannula 112 is retracting from the initial target of the injection site.

(d) Cannula Retraction: This parameter reflects the retraction that the cannula 112 will perform at the end of the operation.

(e) Pause after Insertion: This parameter reflects the time the cannula 112 will pause after the insertion to the target.

(f) Pause after Injection: This parameter reflects the time the cannula 112 will pause after each implant.

(g) Rotation 1, Rotation 2, . . . Rotation n: These parameters indicate the time in milliseconds (or the angular distance) the cannula 112 will rotate after implant 1, 2, . . . n.

Figure 6:
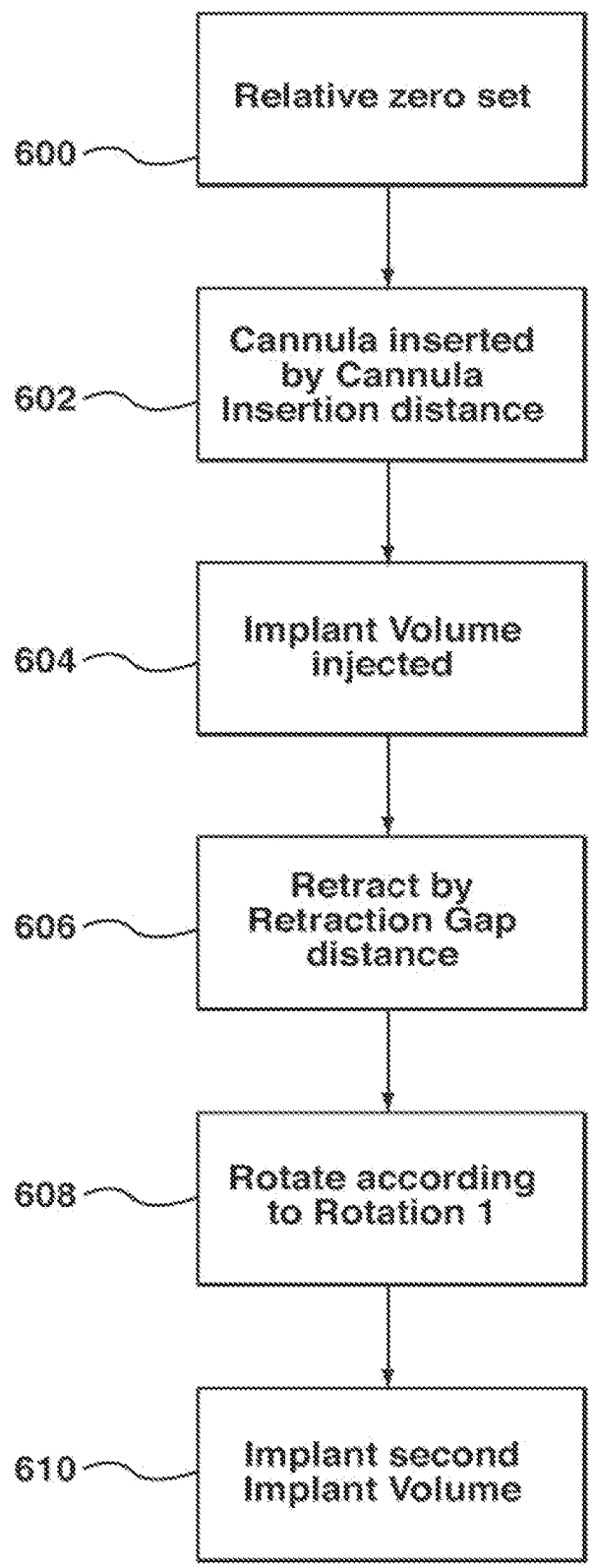
FIG. 6 is a flowchart depicting an exemplary instance of operation of an exemplary injection delivery system in accordance with an aspect of the invention.

An example sequence of instructions is shown in the flowchart of FIG. 6. A user may initially be prompted to set a relative zero coordinate (i.e. a reference) at step 600. At step 602, the cannula 112 is inserted by the Cannula Insertion Distance. At step 604, after the Pause after Insertion time (if any), the first implant, in the amount specified by the relevant Implant Volume, is injected. At step 606, after the Pause after Injection time (if any), the cannula 112 is refracted by the Retraction Gap distance. At step 608, the cannula 112 will rotate for Rotation 1 time. Then, at step 610 the second implant may be injected according to the relevant Implant Volume. Additional retraction, injection and rotation steps may of course be undertaken and, after waiting for the Pause after Injection time after the final implant, the cannula 112 will retract by Cannula Retraction distance. Depending on the pattern, the operational parameters such as Implant Volume, Retraction Gap, Rotation and Pause after Injection may be constant across the procedure, or may have varying values depending on the stage of the procedure. For example, the Implant Volume for the implant at one position may be different from the Implant Volume for the implant at another position.

As an alternative to the automated operation described above, the individual operations may be performed by way of instructions manually entered into the user interface of the electronic controller.

Preferably, an injection delivery system 100 according to an aspect of the present invention should weigh less than 1.0 kg so that it can be supported on a Leksell Stereotactic Frame, as is known in the art, and should still more preferably weigh less than 500 grams. Accordingly, components and materials should be selected with this goal in mind.

In addition, because an injection delivery system 100 according to the present invention will be used in a surgical setting, the design of components should facilitate autoclave (steam), gas or other sterilization, and electrical and electronic components should preferably sealed in a watertight compartment or otherwise isolated from surgical fluids. In addition, interconnection (e.g. interface cables) between the relevant actuators (carriage actuator 106, plunger actuator 118, rotation actuator 114) and the electronic controller should maintain sterility of the injection delivery system 100. Further, interface cables between the electronic controller and the relevant actuators (carriage actuator 106, plunger actuator 118, rotation actuator 114) should preferably disconnect for easy cleaning and replacement.

All mechanical components should be designed so that they can be easily cleaned and gas or (preferably) steam sterilized. Any components that are to be assembled for surgery or disassembled for cleaning preferably should require minimal skill and no tools or at least no special tools. For example snaps, screws or sliding mechanisms may be used to connect components. All components should preferably be easily accessed for maintenance and documented for repair and replacement.

One or more currently preferred embodiments have been described by way of example. It will be apparent to persons skilled in the art that a number of variations and modifications can be made without departing from the scope of the invention as defined in the claims.

What is claimed is:

1. A neurosurgery injection delivery system for automatically injecting fluid into an injection site, comprising:
   at least one support element;
   a carriage moveably mounted to the at least one support element so that the carriage can move linearly relative to the at least one support element;
   a motorized carriage actuator operable to cause incremental linear movement of the carriage relative to the at least one support element;
   the carriage having a support structure adapted for removably receiving and carrying a syringe assembly for movement with the carriage;
   a motorized plunger actuator carried by the carriage so as to move with the carriage, the plunger actuator adapted to be operably coupled to a syringe plunger for causing incremental linear movement thereof within a syringe barrel; and
   a motorized rotation actuator carried by the carriage and operable for causing incremental rotation of a syringe cannula relative to the carriage without causing linear movement of the cannula;
   wherein the carriage actuator, the plunger actuator and the rotation actuator are co-operable to deliver fluid with:
      delivery accuracy: about +/−0.1 microliters (100 nanoliters);
      volume feedback accuracy: about 50 nanoliters;
      position accuracy: about 50 micrometers; and
      position feedback accuracy: about 50 nanometers.

2. The neurosurgery injection delivery system of claim 1, further comprising an electronic controller coupled to the carriage actuator, the plunger actuator and the rotation actuator for:
   controlling the carriage actuator by providing the carriage movement instructions via the carriage actuator input;
   controlling the plunger actuator by providing the plunger movement instructions via the plunger actuator input; and
   controlling the rotation actuator by providing the rotation instructions via the rotation actuator input.

3. The injection delivery system of claim 2, wherein the electronic controller includes a user interface.

4. The injection delivery system of claim 3 wherein the user interface is a touch screen device.

5. The injection delivery system of claim 2, wherein the carriage movement instructions, the plunger movement instructions, and the rotation instructions are stored on a computer readable medium accessible by the electronic controller.

6. The injection delivery system of claim 2, wherein the carriage movement instructions, the plunger movement instructions and the rotation instructions are derived from:
   (a) a volume of fluid to impart from a cannula;
   (b) an insertion distance that the cannula is to move in relation to the at least one support element in the direction of an injection site;
   (c) a retraction distance that the cannula is to retract in relation to the at least one support element from the injection site;
   (d) a rotation amount that the cannula is to rotate in relation to the carriage after a particular injection; and
   (e) a pause time that the cannula will remain still after a particular injection.

* * * * *